United States Patent

Sebag et al.

[11] Patent Number: 5,180,584
[45] Date of Patent: Jan. 19, 1993

[54] WASHING COMPOSITIONS BASED ON INSOLUBLE SILICONES AND ON A SURFACE-ACTIVE AGENT OF THE POLYOXYALKYLENATED CARBOXYLIC ETHER ACID TYPE, AND THEIR APPLICATION IN COSMETICS AND IN DERMATOLOGY

[75] Inventors: Claude Sebag, Paris; Claude Dubief, Le Chesnay, both of France

[73] Assignee: L'Oreal, Paris, France

[21] Appl. No.: 648,848

[22] Filed: Jan. 31, 1991

[30] Foreign Application Priority Data

Jan. 31, 1990 [FR] France ................................ 90 01149

[51] Int. Cl.⁵ ........................ A61K 7/075; A61K 7/48
[52] U.S. Cl. ..................................... 424/401; 424/70;
424/78.02; 514/63; 514/937; 252/DIG. 5
[58] Field of Search ........................... 424/70, 71, 401

[56] References Cited

U.S. PATENT DOCUMENTS

| | | | |
|---|---|---|---|
| 4,563,347 | 1/1986 | Starch | 424/70 |
| 4,601,902 | 7/1986 | Fridd | 424/70 |
| 4,749,565 | 6/1988 | Grollier | 424/71 |
| 4,906,459 | 3/1990 | Cobb | 424/78 |
| 4,925,659 | 5/1990 | Grollier et al. | 424/78 |
| 5,009,880 | 4/1991 | Grollier | 424/78 |
| 5,045,310 | 9/1991 | Halloran | 424/71 |
| 5,049,377 | 9/1991 | Lamb | 424/71 |

FOREIGN PATENT DOCUMENTS 0095238 11/1983 European Pat. Off. .
0331915 9/1989 European Pat. Off. .

Primary Examiner—Thurman K. Page
Assistant Examiner—Raj Bawa
Attorney, Agent, or Firm—Jacobson, Price, Holman & Stern

[57] ABSTRACT

The invention relates to washing compositions based on insoluble silicones, containing in an aqueous medium:
a) a silicone insoluble in the said medium;
b) at least 7% by weight of a compound corresponding to the formula:

$$R-(OC_3H_6)_p-(OC_2H_4)_n-OCH_2-COOA \qquad (I)$$

where
R denotes an alkyl or alkenylradical or a mixture of such radicals, and alkylphenyl or R'CONH—CH$_2$—CH$_2$—, with R' denoting alkyl or alkenyl;
n has the value 2 to 24;
p has the value 0 to 6;
A denotes hydrogen, Na, K, Li, ½ Mg, monoethanolamine, ammonium or triethanolamine; the ratio of compound of formula (I)/silicone being higher than 1;
and their application in cosmetics and in dermatology.

35 Claims, No Drawings

WASHING COMPOSITIONS BASED ON INSOLUBLE SILICONES AND ON A SURFACE-ACTIVE AGENT OF THE POLYOXYALKYLENATED CARBOXYLIC ETHER ACID TYPE, AND THEIR APPLICATION IN COSMETICS AND IN DERMATOLOGY

The invention relates to washing compositions based on insoluble silicones and on a surface-active agent of the polyoxyalkylenated carboxylic ether acid type or its salts, and their application in cosmetics and in dermatology.

Silicone oils are already employed in cosmetics as lubricants in compositions for the treatment of hair or skin. Most of them are insoluble in water and are difficult to utilize.

The Applicant has surprisingly discovered that it is possible to obtain washing compositions based on water-insoluble silicones, by employing as a dispersing and detergent agent a polyoxyalkylenated carboxylic ether acid or one of its salts.

The subject of the invention is therefore new washing compositions, for cosmetic or dermatological use, based on water-insoluble silicones and on at least one surface-active agent of the polyoxyalkylenated carboxylic ether acid type or its cosmetically acceptable salts. These compositions are particularly stable.

Another subject of the invention is processes for washing and/or conditioning hair or the skin, utilizing these compositions.

Further subjects will become apparent on reading the description and the examples which follow.

The present invention relates to a washing composition for the skin or hair, characterised in that it comprises, in an aqueous medium:

a) a silicone which is insoluble in the said medium and not reactive with the latter;

b) at least 7% by weight of a polyoxyalkylene carboxylic ether acid surfactant corresponding to the following formula:

$$R-(OC_3H_6)_p-(OC_2H_4)_n-OCH_2COOA \quad (I)$$

in which:

R denotes a linear or branched, $C_8-C_{22}$ alkyl or alkenyl radical or mixture of such radicals, alkyl($C_8-C_9$)phenyl or R'CONH—CH$_2$—CH$_2$—, with R' denoting a $C_{11}-C_{21}$ linear or branched, alkyl or alkenyl radical;

n is a whole or decimal number between 2 and 24, p is a whole or decimal number between 0 and 6, A denotes a hydrogen atom or else Na, K, Li, ½ Mg or a monoethanolamine, ammonium or triethanolamine residue, the weight ratio of compound of formula (I)/insoluble silicone being higher than 1 and preferably higher than or equal to 1.5.

The silicones employed in accordance with the present invention are polyorganosiloxanes containing no quaternary ammonium group, insoluble in aqueous media and which can be in the form of oils, waxes, gums or resins.

Organopolysiloxanes are defined in greater detail in the work by Walter Noll "Chemistry and Technology of Silicones" (1968) Academic Press.

These silicones must not be reactive with the said media.

The polyorganosiloxanes more particularly employed in accordance with the invention are chosen from volatile silicones which have a boiling point of between 60° C. and 260° C., or else nonvolatile silicones chosen in particular from polyalkylsiloxanes, polyarylsiloxanes, polyalkylarylsiloxanes, silicone gums and resins, organo-modified polysiloxanes and mixtures thereof.

The volatile silicones are more particularly chosen from:

(i) cyclic silicones containing from 3 to 7, and preferably 4 to 5, silicon atoms. They are, for example, octamethylcyclotetrasiloxane sold by Union Carbide under the name Volatile Silicone 7207 or by Rhône-Poulenc as Silbione 70045 V 2, decamethylcyclopentasiloxane sold by Union Carbide under the name Volatile Silicone 7158, Silbione 70045 V 5 from Rhône-Poulenc, and mixtures thereof.

Also mentioned are cyclocopolymers of the dimethylsiloxane/methylalkylsiloxane type, such as Silicone Volatile FZ 3109 sold by Union Carbide, of chemical structure:

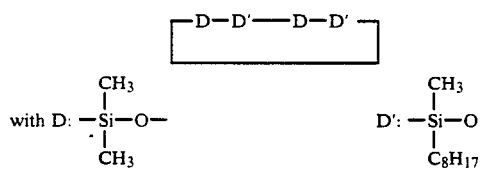

It is also possible to mention the mixtures of cyclic silicones with organic compounds derived from silicon, such as the mixture of octamethylcyclotetrasiloxane and of tetratrimethylsilylpentaerythritol (50/50) and the mixture of octamethylcyclotetrasiloxane and of 1,1'-oxy(2,2,2',2',3,3'-hexatrimethylsilyloxy)bisneopentane;

(ii) linear volatile silicones containing 2 to 9 silicon atoms and having a viscosity lower than or equal to $5 \times 10^{-6}$ m$^2$/s at 25° C. These involve, for example, hexamethyldisiloxane sold under the name Silbione 70 041 V 0.65 by Rhône-Poulenc, decamethyltetrasiloxane sold under the name SH 200 by Toray Silicone or volatile polymethylphenylsilicones such as the product Siliconol AS sold by Wacker. Silicones which are members of this class are also described in the article published in Cosmetics and Toiletries, Vol. 91, Jan. 76, p. 27–32 —Todd & Byers "Volatile Silicone fluids for cosmetics".

The nonvolatile silicones are chosen especially from polyalkylsiloxanes. The chief ones which may be mentioned are linear polydimethylsiloxanes containing trimethylsilyl end groups with a viscosity of $5 \times 10^{-6}$ to 2.5 m$^2$/s at 25° C. and preferably $10^{-5}$ to 1 m$^2$/s, such as, for example, and without any limitation being implied:

the Silbione oils of the 47 and 70 047 series, marketed by Rhône-Poulenc, such as the oil 47 V 500,000, oils of the 200 series from Dow Corning, Viscasil oils from General Electric and some oils of the SF series from General Electric (SF 96, SF 18).

Linear polydimethylsiloxanes with dimethylsilanol end groups are also mentioned, such as the oils of the 48 series from Rhône-Poulenc.

In this class of polyalkylsiloxanes there may also be mentioned polyalkylsiloxane waxes sold by Goldschmidt under the names Abil Wax 9800 and Abil Wax 9801, which are polyalkyl($C_1-C_{20}$)siloxanes.

Among polyalkylarylsiloxanes there may be mentioned poly(dimethylmethylphenylsiloxanes), polymethylphenylsiloxanes, and linear and/or branched polydimethyldiphenylsiloxanes, with a viscosity of $10^{-5}$ to $5\times10^{-2}$ m$^2$/s at 25° C., such as, for example:

Rhodorsil 763 oil from Rhône-Poulenc,

Rhodorsil oils of the 70 633 series from Rhône-Poulenc, such as Rhodorsil 70 633 V 30 oil, Silbione oils of the 70 641 series from Rhône-Poulenc, such as Silbione 70 641 V 30 and 70 641 V 200 oil, the product DC 556 Cosmetic Grad Fluid from Dow Corning, the silicones of the PK series from Bayer, such as PK20, the silicones of the PN and PH series from Bayer, such as PN 1000 and PH 1000, some oils from the SF series from General Electric, such as SF 1250, SF 1265, SF 1154 and SF 1023.

The silicone gums in accordance with the present invention are polydiorganosiloxanes of high molecular masses, of between 200,000 and 1,000,000, employed by themselves or mixed in a solvent chosen from volatile silicones such as defined above, polydimethylsiloxane (PDMS) oil, polyphenylmethylsiloxane (PPMS) oils, isoparaffins, methylene chloride, pentane, dodecane, tridecane, tetradecane or mixtures thereof.

The following gums are mentioned, for example:
poly[(dimethylsiloxane)/(methylvinylsiloxane)],
poly[(dimethylsiloxane)/(diphenylsiloxane)],
poly[(dimethylsiloxane)/(phenylmethylsiloxane)],
poly[(dimethylsiloxane)/(diphenylsiloxane)/(methylvinylsiloxane)]

The following mixtures may be mentioned, for example, no limitation being implied:

the mixtures made up from a polydimethylsiloxane hydroxylated at a chain end (Dimethiconol according to CTFA nomenclature) and from a cyclic polydimethylsiloxane (Cyclomethicone according to CTFA nomenclature), such as the product Q2 1401 sold by Dow Corning, the mixtures made up from a polydimethylsiloxane gum with a cyclic silicone, such as the product SF 1214 Silicone Fluid from General Electric, which is an SE 30 gum corresponding to a Dimethicone sold by General Electric, with a molecular weight of 500,000, dissolved in SF 1202 Silicone Fluid (corresponding to decamethylcyclopentasiloxane), the mixtures of two PDMSs of different viscosities, especially of a PDMS gum and of a PDMS oil, such as the products SF 1236 and CF 1241 from General Electric. The product SF 1236 is a mixture of an SE 30 gum defined above, with a viscosity of 20 m$^2$s, and of an SF 96 Silicone Fluid oil with a viscosity of $5\times10^{-6}$ m$^2$/s (15% of SE 30 gum and 85% of SF 96 oil). The product CF 1241 is a mixture of an SE 30 gum (33%) and of a PDMS oil (67%) with a viscosity of $10^{-3}$ m$^2$/s.

The organopolysiloxane resins in accordance with the present invention are crosslinked siloxane systems containing the units R'$_2$SiO$_{2/2}$, R'SiO$_{3/2}$ and SiO$_{4/2}$, in which R' denotes a hydrocarbon group containing 1 to 6 carbon atoms or a phenyl group.

Particularly preferred among these products are those in which R' denotes a lower alkyl or phenyl radical.

Among these resins there may be mentioned the product sold under the name Dow Corning 593 or those sold under the names Silicone Fluid SS 4230 and SS 4267 from General Electric, which are dimethyl/trimethylpolysiloxanes.

Organomodified silicones in accordance with the present invention are silicones such as defined above, comprising in their general structure one or more organofunctional groups attached directly to the siloxane chain or attached by means of a hydrocarbon radical.

Silicones containing the following are mentioned:

1 polyethyleneoxy and/or polypropyleneoxy groups, optionally containing alkyl groups, such as:

the product called dimethicone copolyol, sold by Dow Corning under the name DC 1248, and the alkyl(C$_{12}$)-methicone copolyol sold by Dow Corning under the name Q2 5200, the Silwet L 722, L 7500, L 77 and L 711 oils from Union Carbide.

a mixture of dimethicone copolyol and of cyclomethicone, such as the product sold under the name Q2-3225C by Dow Corning, 2 amine groups, substituted or otherwise, as in GP4 Silicone Fluid from Genesee, GP 7100 from Genesee or the products sold under the names Q2 8220 and Q2 8200 by Dow Corning. The substituted amine groups are in particular aminoalkyl(C$_1$-C$_4$) groups, 3 thiol groups, as in the products GP 72 A and GP 71 from Genesee or in the product SLM 50253/5 from Wacker, 4 carboxylate groups, as in the case of the products described in Chisso Corporation's European Patent EP-A-186,507, 5 hydroxyl groups, like polyorganosiloxanes containing a hydroxyalkyl functional group, described in French Patent Application No. FR-85/16,334, corresponding to the following formula:

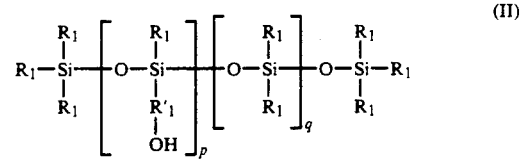

in which:

the radicals R$_1$, which are identical or different, are chosen from methyl and phenyl radicals, at least 60 mol % of the radicals R being methyl;

the radical R'$_1$ is a C$_2$-C$_{18}$ divalent alkylene hydrocarbon chain unit;

p is between 1 and 30 inclusive;

q is between 1 and 150 inclusive.

For example, the product 71 615 V 300, sold by Rhône-Poulenc is mentioned.

6 alkoxy groups, like the product sold under the name Silicone Copolymer F-755 by SWS Silicones and Abil Wax 2428, 2434 and 2440 by Goldschmidt, 7 acyloxyalkyl groups, like, for example, the polyorganosiloxanes described in French Patent Application No. FR-2,641,185, corresponding to the following formula

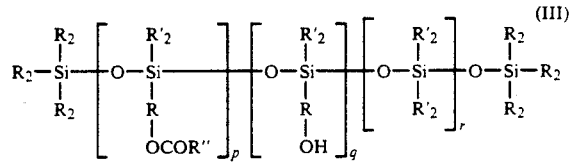

in which:

$R_2$ denotes methyl, phenyl, —OCOR″ or hydroxyl, only one $R_2$ per silicon atom may be OH;

$R'_2$ denotes methyl, phenyl, at least 60 mol % of the total of the radicals $R_2$ and $R'_2$ is methyl;

R″ denotes $C_8-C_{20}$ alkyl or alkenyl;

R denotes a $C_2-C_{18}$, linear or branched, divalent alkylene hydrocarbon;

r is between 1 and 120 inclusive;

p is between 1 and 30;

q has the value of 0 or is smaller than 0.5 p, p+q being between 1 and 30; the polyorganosiloxanes of formula (III) may contain

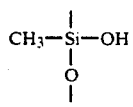

groups in proportions not exceeding 15% of the sum p+q+r.

The compounds of formula (III) can be prepared by esterification of polyorganosiloxanes containing a hydroxyalkyl functional group of formula (II) above.

The esterification is carried out in a known manner, with an acid R″COOH or the corresponding acid anhydride, at a temperature of between 100° and 250° C., optionally in the presence of a catalyst like aluminium chloride or zinc chloride and of a strong acid like hydrochloric acid or sulphuric acid.

It is also possible to carry out a transesterification by heating to 100°-150° C. a methyl ester of formula R″COOCH$_3$ and a diorganopolysiloxane of formula (II) in the presence of an acidic catalyst like para-toluenesulphonic acid or an acidic earth of the montmorillonite type (Katalysator KSF/O, sold by Süd-Chemie - A. G. München).

8 2-hydroxyalkylthiosulphate groups as in the products sold by Goldschmidt under the names Abil S 201 and Abil S 255.

9 Anionic groups of carboxylic type, such as the alkylcarboxylic groups like those present in the product X-22-3701E from Phin-Etsu or in the product Silicone Fluid FZ 3703 from Union Carbide; 2-hydroxyalkylsulphonate.

The polyoxyalkylenated carboxylic ether acids employed in accordance with the invention are preferably chosen from compounds of formula (I) in which R denotes a $C_{12}-C_{14}$ alkyl, oleyl, cetyl or stearyl radical or mixture of such radicals, a nonylphenyl or octylphenyl radical, A denotes a hydrogen or sodium atom and p=0. n varies from 2 to 20 and preferably from 2 to 10.

The commercial products sold by Chem Y under the following names are preferably employed:

Akypo NP 70 (R=nonylphenyl, n=7, p=0, A=H)
Akypo NP 40 (R=nonylphenyl, n=4, p=0, A=H),
Akypo OP 40 (R=octylphenyl, n=4, p=0, A=H)
Akypo OP 80 (R=octylphenyl, n=8, p=0, A=H)
Akypo OP 190 (R=octlphenyl, n32 19, p=0, A=H)
Akypo RLM 25 (R=$C_{12}-C_{14}$ alkyl, n=2.5, p =0, A =H),
Akypo RLM 38 (R=$C_{12}-C_{14}$ alkyl, n=3.8, p =0, A =H),
Akypo RLMQ 38 NV (R=$C_{12}-C_{14}$ alkyl, n=4, p=0, A=Na)
Akypo RLM 45 (R=$C_{12}-C_{14}$ alkyl, n=4.5, p=0, A=H)
Akypo RLM 45 NV (R=$C_{12}-C_{14}$ alkyl, n=5, p=0, A=Na)
Akypo RLM 100 (R=$C_{12}-C_{14}$ alkyl, n=10, p=0, A=H)
Akypo RLM 130 (R=$C_{12}-C_{14}$ alkyl, n=13, p=0, A=H)
Akypo RLM 160 NV (R=$C_{12}-C_{14}$ alkyl, n=16, p=0, A=Na)
Akypo RO 20 (R=oleyl, n=2, p=0, A=H)
Akypo RO 90 (R=oleyl, n=9, p=0, A=H)
Akypo RCS 60 (R=cetyl/stearyl, n =6, p=0, A=H)
Akypo RS 60 (R=stearyl, n=6, p=0, A=H)
Akypo RS 100 (R=stearyl, n=10, p=0, A=H)
Akypo RO 50 (R=oleyl, n=5, p=0, A=H)

or by Sandoz under the names:

Sandopan ACA-48 (R=cetyl/stearyl, n=24, p=0, A=H)
Sandopan DTC Acid (R=$Cu_{13}$ alkyl, n=6, p=0, A=H)
Sandopan DTC (R=$C_{13}$ alkyl, n=6, p=0, A=Na)
Sandopan LS-24 (R=$C_{12}-C_{14}$ alkyl, n=12, p=0, A=Na)
Sandopan JA-36 (R=$Cu_{13}$ alkyl, n=18, p=0, A=H)

and more particularly the products sold under the following names:

Akypo NP 70
Akypo NP 40
Akypo OP 40
Akypo OP 80
Akypo RLM 25
Akypo RLM 45
Akypo RLM 100
Akypo RO 20
Akypo RO 50
Akypo RLM 38.

In the compositions in accordance with the invention the compounds of formula (I) are present in proportions of between 7% and 50% and preferably between 8% and 30% relative to the total weight of the compositions.

The silicones are present in proportions of between 0.2 and 30% and preferably between 0.2 and 10% relative to the total weight of the compositions.

The cosmetic compositions according to the invention may be employed in particular as shampoos, washing cream, in the form of shower gels or of foam baths for the body.

The cosmetic or dermatological compositions in accordance with the present invention may additionally contain other surface-active agents differing from those of formula (I) and chosen from anionic, amphoteric, zwitterionic or nonionic surface-active agents or mixtures thereof.

Among the anionic surfactants there may be mentioned more particularly: the alkali metal salts, the ammonium salts, the amine salts or the aminoalcohol salts of the following compounds:

alkyl sulphates, alkyl ether sulphates, alkyl amidesulphates and ether sulphates, alkanolamide sulphates, alkylaryl polyether sulphates, monoglyceride sulphates, alkylsulphonates, alkylamidesulphonates, alkylarylsulphonates, olefinsulphonates, paraffinsulphonates, alkylsulphosuccinates, alkyl ether sulphosuccinates, alkylamidesulphosuccinates, alkylsulphosuccinamates, alkylsulphoacetates,
acylsarcosinates, acylpolypeptidates, acylamidopolypeptidates, acylisethionates, N-acyltaurates;
the alkyl or acyl radical of these compounds consisting of a carbon chain containing 8 to 18 carbon atoms.

Among the anionic surface-active agents there may also be mentioned:
salts of fatty acids such as oleic, ricinoleic, palmitic and stearic acids, and the copra or hydrogenated copra oil acids,
acyl lactylates in which the acyl radical contains 8 to 20 carbon atoms.

Among the nonionic surface-active agents there may be mentioned in particular: polyoxyethylenated, polypropoxylated or polyglycerolated alcohols, alkylphenols and fatty acids with a fatty chain containing 8 to 18 carbon atoms, the number of ethylene oxide or propylene oxide groups being between 2 and 50 and the number of glycerol groups being between 2 and 30.

There may also be mentioned copolymers of ethylene and propylene oxides, condensates of ethylene and propylene oxides with fatty alcohols, polyethoxylated fatty amides (preferably from 2 to 30 moles of ethylene oxide), ethanolamides, glycol fatty acid esters, sorbitan fatty acid esters, oxyethylenated (preferably from 2 to 30 moles of ethylene oxide) or otherwise, sucrose fatty acid esters, polyethylene glycol fatty acid esters, fatty acid esters of glucose derivatives, polyethoxylated fatty amines (preferably from 2 to 30 moles of ethylene oxide), amine oxides such as alkylamine oxides or N-acylamidopropylmorpholine.

The preferred oxyethylenated or polyglycerolated fatty alcohols are oleyl alcohol oxyethylenated with 10 moles of ethylene oxide, lauryl alcohol oxyethylenated with 12 moles of ethylene oxide, nonylphenol oxyethylenated with 9 moles of ethylene oxide, oleyl alcohol polyglycerolated with 4 moles of glycerol; the preferred polyoxyethylenated sorbitan fatty acid ester is sorbitan monolaurate polyoxyethylenated with 20 moles of ethylene oxide.

Other compounds included in this class are poly(hydroxypropyl)ether compounds corresponding to the formulae (IV) to (VI) below and/or prepared according to the processes described below:

(1) 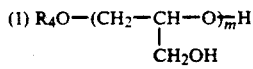 (IV)

in which $R_4$ denotes an alkyl radical or a mixture of alkyl radicals containing 10 to 14 carbon atoms and m is a whole or decimal number from 2 to 10 and preferably from 3 to 6. These compounds of formula (IV) can be prepared according to the process described in patent FR-A-1,477,048;

(2)
$R_5$—CONH—$CH_2$—$CH_2$—O—$CH_2$—$CH_2$O—($CH_2$—CHOH—$CH_2$—O$)_n$H (V)

in which $R_5$ denotes an alkyl and/or alkenyl radical containing from 11 to 17 carbon atoms or a mixture of such radicals and n denotes a whole or decimal number from 1 to 5 and preferably 1.5 to 4. These compounds of formula (V) can also be prepared according to the process described in Patent FR-A-2,328,763;

(3) $R_6$—CHOH—$CH_2$—O—($CH_2$—CHOH—$CH_2$—O$)_p$H (VI)

in which $R_6$ denotes an aliphatic, cycloaliphatic or arylaliphatic radical preferably containing 7 to 21 carbon atoms, and mixtures thereof, the aliphatic chains denoting in particular alkyl chains which may contain 1 to 6 ether, thioether and/or hydroxymethylene groups, and p is between 1 and 10 inclusive.

These compounds are prepared by condensation, using alkaline catalysis, of 2 to 10 and preferably of 2.5 to 6 moles of glycidol with a $C_{10}$–$C_{14}$ alpha-diol or a mixture of such alpha-diols, at a temperature of 120°–180° C. and preferably of 140° to 160° C., the glycidol being added slowly according to the preparative process described in patent FR-A-2,091,516;

(4) the compounds prepared by condensation, using acidic catalysis, of 2 to 10 and preferably 2.5 to 6 moles of glycidol per mole of alcohol or of alpha-diol containing 10 to 14 carbon atoms at a temperature of 50° to 120° C., the glycidol being added slowly to the alcohol or to the alpha-diol. The process for the preparation of these compounds is described more particularly in patent FR-A-2,169,787;

(5) the poly(hydroxypropyl)ether compounds prepared by polyaddition of glycerol monochlorohydrin to a (poly)hydroxylated organic compound in the presence of a strong base, with progressive removal of water by distillation, these being described in particular in French Patent FR-A-2,574,786.

Among the nonionic surfactants of the poly(hydroxypropyl)ether class described in paragraphs (1), (2), (3), (4) and (5) above, the preferred compounds are denoted by the formulae:

(α) 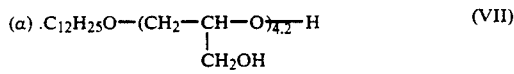 (VII)

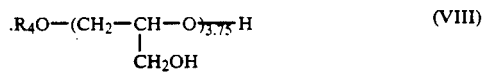 (VIII)

where $R_4$ denotes a mixture of $C_{10}H_{21}$ and $C_{12}H_{25}$ alkyl radicals;

(β) the compounds prepared by condensation, using alkaline catalysis, of 3.5 moles of glycidol with an alpha-diol containing 12 carbon atoms, according to the process described in patent FR-A-2,091,516;

(γ) the compounds corresponding to the formula:

$R_6$—CONH—$CH_2$—$CH_2$—O—$CH_2$—$CH_2$—O—($CH_2$—CHOH—$CH_2$—O$)_{3.5}$H (IX)

where $R_6$ denotes a mixture of radicals containing the following alkyl and alkenyl radicals: $C_{11}H_{23}$, $C_{13}H_{27}$, the radicals derived from copra fatty acids and the radical derived from oleic acid;

(δ) the compounds prepared by condensing 3.5 moles of glycidol with a mixture of $C_{11}$–$C_{14}$ alpha-diols, described in patent FR-A-2,091,516, the poly(hydroxypropyl)ether nonionic surfactant obtained by condensing glycerol monochlorohydrin (2.5 moles) in the presence of sodium hydroxide with 1,2-dodecanediol are more particularly preferred.

Among the amphoteric and zwitterionic surface-active agents which may be employed there may be mentioned, for example:

1. derivatives of aliphatic secondary or tertiary amines in which the aliphatic radical is a linear or branched chain containing from 6 to 18 carbon atoms and which contains at least one water-soluble carboxylic, sulphonate, sulphate, phosphate or phosphonate anionic group.

Among these compounds more particular mention may be made of the products sold under the name Miranol, described in patents U.S. Pat. Nos. 2,528,378 and 2,781,354 and classified in the CTFA Dictionary, 3rd edition, 1982, under the name of Amphocarboxyglycinates and Amphocarboxypropionates.

These products have the following structures: Amphocarboxyglycinate

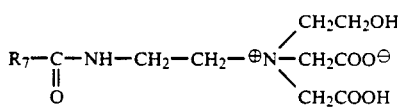

in which $R_7$ denotes an alkyl radical derived from copra, a heptyl, nonyl or undecyl radical;

Amphocarboxypropionate

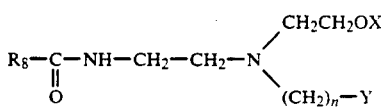

in which:
n has the value 1 or 2;
X denotes the —$CH_2CH_2COOH$ group or hydrogen;
Y denotes —COOH or the radical

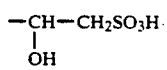

$R_8$ denotes an alkyl radical derived from copra, a $C_7$, $C_8$, $C_{11}$ or $C_{13}$ alkyl radical, a $C_{17}$ alkyl radical and its iso form, an unsaturated $C_{17}$ radical, or an alkyl radical derived from linseed oil;

2. alkylbetaines, sulphobetaines, amidobetaines and amidosulphobetaines.

The alkylbetaines are preferably chosen from alkyl($C_{10}$-$C_{20}$)betaines.

In accordance with the present invention, mixtures of surfactants are preferably employed in combination with the compounds of formula (I), and preferably mixtures consisting of anionic surfactants or mixtures consisting of anionic surfactants coupled with amphoteric, zwitterionic or nonionic surface-active agents.

Use is preferably made of one or more anionic surface-active agents chosen from sodium, triethanolamine or ammonium $C_{12}$-$C_{14}$ alkylsulphonates, sodium $C_{12}$-$C_{14}$ alkyl ether sulphates oxyethylenated with 2.2 moles of ethylene oxide, sodium cocoylisethionate, sodium $C_{14}$-$C_{16}$ α-olefinsulphonate, sodium lauroylsarcosinate and mixtures thereof with either an amphoteric surfactant such as an amphocarboxyglycinate defined by the above formula, in which $R_7$ denotes an alkyl radical derived from copra, called Cocoamphocarboxyglycinate, sold by Miranol under the trade name Miranol C2M CONC;

or a zwitterionic surfactant such as the laurylbetaine sold by Henkel under the trade name Dehyton AB 30;

or a nonionic surfactant of formulae (IV), (V), (VI) above or an alkylamine oxide.

When amphoteric or zwitterionic surfactants are employed mixed with anionic surfactants, they represent up to 50%, and preferably from 5 to 30%, by weight of the total weight of the quantity of surface-active agents present in the composition.

When nonionic surfactants are employed mixed with anionic surfactants, they represent up to 80%, and preferably from 5 to 50%, of the total weight of the quantity of surface-active agents present in the composition.

The cosmetic or dermatological compositions according to the present invention may be in the form of opaque or clear products.

To obtain opaque compositions, it is preferred to employ silicones chosen from:

silicone oils of high viscosity of between 0.2 and 2.5 $m^2/s$ at 25° C., such as the 47 V 500,000 oils from Rhône-Poulenc.

mixtures of organopolysiloxanes and of cyclic silicones, such as the product Q2 1401 sold by Dow Corning, mixtures of two PDMSs of different viscosities, such as the product sold by General Electric under the name CF 1241, organomodified oils such as silicones containing a γ-hydroxypropyl group, in particular the oil 71 615 V 300 sold by Rhône-Poulenc, or containing an acyloxy and in particular stearoyloxypropyl functional group described above.

To obtain clear products it is preferred to employ, according to the invention, silicones chosen from:

cyclic volatile silicones containing from 3 to 7 silicon atoms, such as the octamethylcyclotetrasiloxane sold under the name Huile Silbione 70045 V 2 from Rhône-Poulenc or the decamethylcyclopentasiloxane sold under the name Volatile Silicone 7158 from Union Carbide or mixtures thereof with organosilicon compounds, PPMS oils of viscosity lower than $5 \times 10^{-5}$ $m^2/s$, such as the oils 70 633 V 30 from Rhône-Poulenc and DC 556 from Dow Corning, linear PDMS oils containing from 2 to 9 silicon atoms and a viscosity lower than $2 \times 10^{-6}$ $m^2/s$, such as the SH 200 oil from Toray Silicone.

Among the above silicones, more particular preference is given to cyclic volatile silicones and to PPMSs of viscosity lower than $5 \times 10^{-5}$ $m^2/s$.

In the case of opaque compositions in accordance with the present invention, use is made more particularly of the compounds of formula (I) in which:
R=octylphenyl
n=4, p=0
A=H This compound is sold under the name Akypo OP 40 by Chem Y as 90% of active substance (AS).
R=nonylphenyl
n=4, p=0
A=H This compound is sold under the name Akypo NP 40 by Chem Y as 90% of AS.
R=oleyl
n=2 or 5, p=0
A=H These compounds are sold under the names Akypo RO 20 and RO 50 by Chem Y as 90% of AS.

R = $C_{12}$–$C_{14}$ alkyl
n = 2.5
A = H

This compound is sold under the name Akypo RLM 25 by Chem Y as 90% of AS.

In the case of the clear compositions in accordance with the present invention, use is made more particularly of the compounds of formula (I), in which:
R = nonylphenyl
n = 7, p = 0
A = H This compound is sold under the name Akypo NP 70 by Chem Y as 90% of AS, or a mixture of these compounds, in which:
R = octylphenyl
n = 4 or 8, p = 0
A = H These compounds are sold under the names Akypo OP 40 and Akypo OP 80 by Chem Y, and
R = lauryl
n = 10, p = 0
A = H this compound being sold under the name Akypo RLM 100 by Chem Y as 90% of AS.

The total quantity of surfactants in these washing compositions is generally between 7 and 50% by weight relative to the total weight of the composition, and in particular between 8 and 30% by weight.

The proportion of additional surfactant does not exceed 40% and is preferably between 0 and 20%.

The cosmetic or dermatological compositions according to the invention have a pH which is generally between 2 and 9.

The compositions according to the invention may be in the form of more or less thickened liquids, gels or aerosol foams.

They may also contain viscosity regulating agents such as electrolytes, hydrotropes or other thickeners, among which there may be mentioned, for example: sodium chloride, sodium xylenesulphonate, cellulose derivatives such as, for example, carboxymethyl cellulose, hydroxypropyl cellulose, guar gum, hydroxypropylated guar gums and scleroglucanes.

These viscosity regulating agents are employed in proportions of up to 15% by weight relative to the total weight of the composition, and preferably of less than 6%.

The compositions in accordance with the invention may optionally additionally contain other agents which have the effect of improving the cosmetic properties of hair and/or of the skin, provided that they do not alter the stability of the compositions, such as cationic surfactants, anionic or cationic polymers or quaternised or unquaternised proteins and water-soluble silicones.

The cationic or anionic polymers, the cationic surfactants and the quaternised or unquaternised proteins are employed in the cosmetic or dermatological compositions according to the invention in proportions of between 0.05 and 6% and preferably between 0.1 and 3% relative to the total weight of the composition.

The water-soluble silicones may be employed in all the compositions according to the invention in proportions ranging up to 10% and preferably between 0.5 and 6% relative to the total weight of the composition.

The compositions according to the invention may also contain various adjuvants which are usually employed in cosmetics, such as perfumes, stabilisers, sequestrants, foam stabilisers, propelling agents, colorants, acidifying or alkalifying agents or other adjuvants, depending on the use which is envisaged.

The dermatological compositions additionally contain an active substance for the treatment of dermatological ailments.

The processes for washing and conditioning hair or the skin consist in applying thereto a composition as defined above and chosen according to the treatment which is envisaged, this application being followed by a rinsing.

The examples which follow illustrate the present invention without, however, limiting it.

EXAMPLES 1 TO 5

Shampoos of the following compositions are prepared:

TABLE 1

| in g AS | 1 | 2 | 3 | 4 | 5 |
|---|---|---|---|---|---|
| Akypo NP 70 cont. 90% of AS | 18 | | 13.5 | 9 | 10.8 |
| Akypo OP 40 cont. 90% of AS | | | | 4.5 | |
| Akypo RO 20 cont. 90% of AS | | 3.6 | | | |
| Akypo RO 90 cont. 90% of AS | | 3.6 | | | |
| 47 V 500,000 RP oil | | | | | 1 |
| Silbione 70 047 V 300 RP | 10 | 2 | | | |
| Silbione 70 633 V 30 Rhone-Poulenc | | | | | 2 |
| Mixture of a dimethiconol and of a cyclomethicone sold under the name Q2-1401 by Dow Corning | | | 1 | | |
| Water q.s. | 100 | 100 | 100 | 100 | 100 |
| Triethanolamine q.s. pH | 4 | | | | |
| Spontaneous pH | | 2.7 | 2.2 | 2.2 | 2.3 |

EXAMPLES 6 TO 12

Clear shampoos are prepared, whose compositions are shown in Table 2:

EXAMPLES 13 TO 19

Opaque shampoos are prepared, whose compositions are shown in Table 3:

TABLE 2

| | Clear shampoos | | | | | | |
|---|---|---|---|---|---|---|---|
| in g AS | 6 | 7 | 8 | 9 | 10 | 11 | 12 |
| Akypo NP 70 | 9 | 9 | 9 | | 7.2 | 9 | 9 |
| Akypo OP 40 | | | | 6.3 | | | |
| Akypo OP 80 | | | | 9 | | | |
| Akypo RLM 100 | | | | 2.7 | | | |
| Decamethylcyclopentasiloxane sold by Union Carbide under the name Volatile Silicone 7158 | 2.5 | | | | | | |
| Decamethyltetrasiloxane sold by Toray Silicone under the name | | 2.5 | | | | | |

TABLE 2-continued

| in g AS | Clear shampoos | | | | | | |
|---|---|---|---|---|---|---|---|
| | 6 | 7 | 8 | 9 | 10 | 11 | 12 |
| SH 200 | | | | | | | |
| 70 633 V 30 oil (Rhone-Poulenc) | | | | 5 | 2 | | |
| Mixture of $D_4$ and of silicon compound (1) | | | | | | | 2.5 |
| Mixture of $D_4$ and of silicon compound (2) | | | 2.5 | | | 2.5 | |
| Dimethicone copolyol sold as 35% of AS by Goldschmidt under the name Huile CL 183/25 | | | | | | | |
| Sodium $C_{12}$-$C_{14}$ alkyl ether sulphate oxyethylenated with 2.2 moles of ethylene oxide, sold as 25% of AS | 10 | 10 | | | | | |
| Triethanolamine alkyl($C_{12}$-$C_{14}$/70-30) sulphate in aqueous solution cont. 40% of AS | | | 10 | 10 | 10 | 4 | 12 |
| Laurylbetaine in aqueous solution cont. 32% of AS, sold under the name Dehyton AB 30 by Henkel | | | | | | | 3 |
| Sodium lauroylsarcosinate sold as aqueous solution cont. 30% of AS by Seppic under the name Oramix L30 | | | | | 4 | | |
| Poly(hydroxypropyl ether) nonionic surfactant prepared by condensation, using alkaline catalysis, of 3.5 moles of glycidol with an alpha-diol containing 12 carbon atoms, according to the process described in patent FR-A-2,091,516 | | | | | | 4 | |
| Polymer of hydroxyethyl cellulose and epichlorohydrin, quaternised with trimethylamine, sold under the name JR 400 by Union Carbide | | | | | 1 | | |
| Copra acid diethanolamide | 2.5 | 2.5 | 2.5 | | | 2.5 | 2.5 |
| Sodium chloride | 4 | 4 | 2.5 | | | | |
| Triethanolamine q.s. pH | 7.2 | 7.2 | 8 | 7 | 6 | 4 | |
| Spontaneous pH | | | | | | | 3.6 |
| Stabilisers, perfumes | q.s. | q.s. | q.s. | q.s. | q.s. | q.s. | q.s. |
| Water q.s. | 100 | 100 | 100 | 100 | 100 | 100 | 100 |

(1) Mixture of octamethylcyclotetrasiloxane ($D_4$) and of tetratrimethylsilylpentaerythritol.
(2) Mixture of octamethylcyclotetrasiloxane ($D_4$) and of 1,1'-oxy(2,2,2',2',3,3'-hexatrimethylsilyloxy)-bisneopentane.

TABLE 3

| in g AS | Opaque shampoos | | | | | | |
|---|---|---|---|---|---|---|---|
| | 13 | 14 | 15 | 16 | 17 | 18 | 19 |
| Akypo NP 70 | 9 | | | | 4.5 | | |
| Akypo OP 40 | | | | 9.7 | | 10.8 | 10.8 |
| Akypo OP 80 | | 36 | | | | | |
| Akypo NP 40 | 4.5 | | 10.8 | | 4.5 | | |
| 47 V 500,000 oil (Rhone-Poulenc) | 1 | | | 1.5 | | | |
| DC 593 silicone sold by Dow Corning | | | | | 0.5 | | |
| Mixture of dimethiconol and of a cyclomethicone sold under the name Q2-1401 by Dow Corning | | | 2 | | | | |
| Mixture of two PDMs of different viscosities, sold under the name CF 1241 by General Electric | | | | | | 3 | |
| 47 V 300 oil (Rhone-Poulenc) | | 0.5 | | | | | |
| Silbione 71615 V 300 oil (Rhone Poulenc) | | | | | | | 2 |
| Sodium cocoylisethionate sold under the name Fenopon AC 78 by GAF | | | 12 | | | | |
| Mixture (84/8 by weight) of sodium cocoylisethionate and sodium isothionate, sold under the name Arlatone SCI by ICI | | 5 | | | | | |
| Sodium laurylsulphate | | | | | 10 | 15 | |
| Ammonium laurylsulphate | | | | 5 | | | |
| Sodium $C_{14}$-$C_{16}$ olefinsulphonate sold as aqueous solution cont. 38% of AS | 5.7 | 7.6 | | | 5 | | |
| Triethanolamine alkyl-($C_{12}$-$C_{14}$/70-30) sulphate as | | | | | | | 10 |

TABLE 3-continued

| in g AS | Opaque shampoos | | | | | | |
|---|---|---|---|---|---|---|---|
| | 13 | 14 | 15 | 16 | 17 | 18 | 19 |
| aqueous solution cont. 40% of AS | | | | | | | |
| Cocoamphocarboxyglycinate sold under the name Miranol C2M Conc. by Miranol as aqueous solution cont. 38% of AS | | | | | 2 | | |
| Laurylbetaine as aqueous solution cont. 32% of AS | 3 | | | | 5 | | |
| Poly(hydroxypropyl ether) nonionic surfactant prepared by condensation. using alkaline catalysis, of 3.5 moles of glycidol with an alpha-diol containing 12 carbon atoms, according to the process described in patent FR-A-2,091,516 | | | | | | 3 | |
| N,N-dimethyl-N-alkyl($C_{11}$-$C_{17}$)-amidopropyl) amine oxide sold as aqueous solution cont. 35% of AS by Goldschmidt under the name Aminoxid WS 35 | | | | | | 0.5 | |
| Quaternised protein sold under the name Lexein QX 3000 by Inolex as 30% of AS | | | | | 0.5 | | |
| Stearyldimethylbenzylammonium chloride | | | 1 | | 1 | | |
| Sodium chloride | | | 3 | 3 | | 3 | 2 |
| Triethanolamine q.s. pH | 5 | | | | | | 4.5 |
| Sodium hydroxide q.s. pH | | | 4 | | | | |
| Spontaneous pH | | 3 | | 3 | 3.1 | 3 | |
| Water q.s. | 100 | 100 | 100 | 100 | 100 | 100 | 100 |

EXAMPLE 20

A foam bath of the following composition is prepared:

| | |
|---|---|
| Akypo RLM 45 cont. 90% of AS | 13.5 g AS |
| 47 V 500,000 oil sold by Rhone-Poulenc | 0.1 g |
| sodium $C_{14}$-$C_{17}$ n-alkylsulphonate sold under the name Hostapur SAS 30 by Hoechst | 18.0 g |
| stabilizer, perfume q.s. | |
| spontaneous pH = 5 | |
| water q.s. | 100.0 g |

EXAMPLE 21

A clear shower gel of the following composition is prepared:

| | |
|---|---|
| Akypo OP 40 cont. 90% of AS | 3.94 g AS |
| Akypo OP 80 cont. 90% of AS | 5.63 g AS |
| Akypo RLM 100 cont. 90% of AS | 1.69 g AS |
| Silbione 70 633 V 30 (PPMS) oil sold by Rhone-Poulenc | 2.5 g |
| triethanolamine $C_{12}$-$C_{14}$ alkylsulphate | 16.0 g AS |
| stabilizer, perfume q.s. | |
| triethanolamine q.s. pH = 7 | |
| water q.s. | 100.0 g |

EXAMPLE 22

A washing cream of the following composition is prepared:

| | |
|---|---|
| Akypo RO 20 sold as 90% of AS by Chem Y | 10.8 g AS |
| Silbione 70 047 V 300 (PDMS) oil sold by Rhone-Poulenc | 10.0 g |
| sodium hydroxide q.s. pH = 5.5 | |
| water q.s. | 100.0 g |

EXAMPLE 23

A shampoo gel of the following composition is prepared:

| | |
|---|---|
| Akypo RO 50 sold as 90% of AS by Chem Y | 5.0 g AS |
| Akypo RO 90 sold as 90% of AS by Chem Y | 20.0 g AS |
| Silbione 70 047 V 500,000 (PDMS) oil sold by Rhone-Poulenc | 5.0 g |
| sodium chloride | 5.0 g |
| sodium hydroxide q.s. pH = 3.7 | |
| water q.s. | 100.0 g |

EXAMPLE 24

A clear foam bath of the following composition is prepared:

| | |
|---|---|
| Akypo RLM 38 sold as 90% of AS by Chem Y | 8.0 g AS |
| sodium alkyl ether sulphate ($C_9$/$C_{11}$/$C_{13}$/$C_{15}$-3/7/63/27%, cont. 50% linear) oxyethylenated with 3 ethylene oxides, sold as aqueous solution cont. 70% of AS by ICI | 21.0 g AS |
| Q2-8200 oil (PDMS cont. amine functional group) sold by Dow Corning | 3.0 g |
| sodium chloride | 3.0 g |
| spontaneous pH = 3.7 | |
| water q.s. | 100.0 g |

We claim:

1. Washing composition for hair or the skin, comprising in an aqueous medium:
   a) a silicone which is insoluble in the said medium and not reactive with the latter; and
   b) at least 7% by weight of at least one compound corresponding to the following formula:

$$R-(OC_3H_6)_p-(OC_2H_4)_n-OCH_2-COOA \qquad (I)$$

in which:
   R denotes a linear or branched, $C_8$-$C_{22}$ alkyl or alkenyl radical or mixture of such radicals, alkyl($C_8$-$C_9$)phenyl or $R'CONH-CH_2-CH_2-$, with R' denoting a $C_{11}$-$C_{21}$, linear or branched, alkyl or alkenyl radical;
   n is a whole or decimal number between 2 and 24,
   p is a whole or decimal number between 0 and 6,
   A denotes a hydrogen atom or an atom of Na, K, Li, ½ Mg or a monoethanolamine, ammonium or triethanolamine residue,
   the weight ratio of compound of formula (I)/insoluble silicone being higher than 1.

2. Composition according to claim 1, in which the silicone is chosen from polyorganosiloxanes containing no quaternary ammonium group, insoluble in aqueous media and not reactive with the latter, which are in the form of oils, waxes, gums or resins.

3. Composition according to claim 1, characterised in that the silicone is a volatile silicone which has a boiling point of between 60° and 260° C., or else a nonvolatile silicone chosen from polyalkylsiloxanes, polyarylsiloxanes, polyalkylarylsiloxanes, modified or unmodified polyethersiloxane copolymers, silicone gums and resins, organomodified polysiloxanes, and mixtures thereof.

4. Composition according to claim 3, in which the volatile silicone is chosen from:
   (i) cyclic silicones containing from 3 to 7, and preferably 4 to 5, carbon atoms, their mixtures with organic compounds derived from silicon, or else cyclocopolymers of following formula:

$$\left[ -D-D'---D-D'- \right]$$

with D:
$$\begin{array}{c} CH_3 \\ | \\ -Si-O- \\ | \\ CH_3 \end{array}$$
D':
$$\begin{array}{c} CH_3 \\ | \\ -Si-O \\ | \\ C_8H_{17} \end{array}$$

(ii) linear silicones containing 2 to 9 silicon atoms and having a viscosity lower than or equal to $5 \times 10^{-6}$ m²/s at 25° C.

5. Composition according to claim 3, in which the nonvolatile silicone is chosen from:
   A) linear polydimethylsiloxanes containing trimethylsilyl end groups, which have a viscosity of $5 \times 10^{-6}$ to 2.5 m²/s at 25° C.;
   B) linear polydimethylsiloxanes containing dimethylsilanol end groups;
   C) polyalkyl($C_1$-$C_{20}$)siloxanes;
   D) linear and/or branched poly(dimethylmethylphenylsiloxanes), polymethylphenylsiloxanes and polydimethyldiphenylsiloxanes with a viscosity of $10^{-5}$ to $5 \times 10^{-2}$ m²/s at 25° C.;
   E) silicone gums of molecular mass of between 200,000 and 1,000,000, employed by themselves or in the form of mixtures in a solvent, chosen from the group consisting of the following copolymers:
   poly[(dimethylsiloxane)/(methylvinylsiloxane)],
   poly[(dimethylsiloxane)/(diphenylsiloxane)],
   poly[(dimethylsiloxane)/(phenylmethylsiloxane)],
   poly[(dimethylsiloxane)/(diphenylsiloxane)/(methylvinylsiloxane)];
   and the following mixtures:
   the mixtures made up from a polydimethylsiloxane hydroxylated at a chain end and from a cyclic polydimethylsiloxane;
   the mixtures made up from a polydimethylsiloxane gum and from a cyclic silicone;
   the mixtures of two polydimethylsiloxanes of different viscosities;
   F) organosiloxane resins which are crosslinked siloxane systems containing $R'_2SiO_{2/2}$, $R'SiO_{3/2}$ and $SiO_{4/2}$ units, in which R' denotes a hydrocarbon group containing from 1 to 6 carbon atoms or a phenyl group;
   G) organomodified silicones chosen from silicones containing in their structure one or more organofunctional groups attached directly to the siloxane chain or attached by means of a hydrocarbon radical.

6. Composition according to claim 5, in which the organomodified silicones are chosen from polyorganosiloxanes containing
   a) polyethyleneoxy and/or polypropyleneoxy groups;
   b) amine groups, substituted or otherwise;
   c) thiol groups;
   d) carboxylate groups;
   e) alkoxy groups;
   f) hydroxyalkyl groups corresponding to the following formula:

$$R_1-\underset{\underset{R_1}{|}}{\overset{\overset{R_1}{|}}{Si}}-\left[O-\underset{\underset{R'_1}{|}}{\overset{\overset{R_1}{|}}{Si}}\right]-\left[O-\underset{\underset{R_1}{|}}{\overset{\overset{R_1}{|}}{Si}}\right]_q-O-\underset{\underset{R_1}{|}}{\overset{\overset{R_1}{|}}{Si}}-R_1 \qquad (II)$$
(with OH on the middle group, subscript p)

in which:
   radicals $R_1$ which are identical or different, are chosen from methyl and phenyl radicals, at least 60 mol % of the radicals $R_1$ being methyl;
   the radical $R'_1$ is a $C_2$-$C_{18}$ divalent alkylene hydrocarbon chain unit;
   p is between 1 and 30 inclusive;
   q is between 1 and 150 inclusive;
   g) acyloxyalkyl groups corresponding to the following formula:

$$R_2-\underset{\underset{R_2}{|}}{\overset{\overset{R_2}{|}}{Si}}-\left[O-Si\right]_p-\left[O-Si\right]_q-\left[O-Si\right]_r-O-\underset{\underset{R_2}{|}}{\overset{\overset{R_2}{|}}{Si}}-R_2 \qquad (III)$$
(with OCOR″ subscript p, OH subscript q, R'_2 groups)

in which:
   $R_2$ denotes methyl, phenyl, $-OCR''$ or hydroxyl, only one $R_2$ per silicon atom may be OH;
   $R'_2$ denotes methyl, phenyl, at least 60 mol % of the total of the radicals $R_2$ and $R'_2$ is methyl;
   R″ denotes $C_8$-$C_{20}$ alkyl or alkenyl;

R denotes a $C_2$-$C_{18}$, linear or branched, divalent alkylene hydrocarbon;

r is between 1 and 120 inclusive;

p is between 1 and 30;

q has the value of 0 or is smaller than 0.5 p. p+q being between 1 and 30; the polyorganosiloxanes of formula (III) may contain

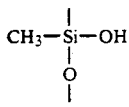

groups in proportions exceeding 15% of the sum p+q+r;

h) anionic groups of the 2-hydroxyalkylthiosulphate, 2-hydroxyalkylsulphonate or alkylcarboxylic type.

7. Composition according to claim 1, characterised in that the compound of formula (I) is chosen from those in which R denotes a $C_{12}$-$C_{14}$ alkyl, oleyl, cetyl or stearyl radical or mixture of such radicals, an octylphenyl or nonylphenyl radical, p is equal to 0 and A denotes a hydrogen or sodium atom.

8. Composition according to claim 1, characterised in that the silicone is present in proportions of between 0.2 and 30% by weight relative to the total weight of the composition.

9. Composition according to claim 1, characterised in that the compound of formula (I) is present in proportions of between 7 and 50% and preferably between 8 and 30% by weight relative to the total weight of the composition.

10. Composition according to claim 1, characterised in that it is in the form of a shampoo, washing cream, shower gel or foam bath.

11. Composition according to anyone of claims 1 to 10, characterised in that it additionally contains an anionic, amphoteric, zwitterionic or nonionic surfactant or mixtures thereof.

12. Composition according to claim 11, in which the anionic surfactant is chosen from:
  a) ammonium salts, alkali metal salts, amine salts or aminoalcohol salts of the following compounds:
    alkylsulphates, alkyl ether sulphates, alkylamide sulphates and ether sulphates, alcanolamide sulphates, alkylaryl polyether sulphates, monoglyceride sulphates,
    alkylsulphonates, alkylamidesulphonates, alkylarylsulphonates, olefinsulphonates, paraffinsulphonates,
    alkylsulphosuccinates, alkyl ethersulphosuccinates, alkylamidesulphosuccinates,
    alkylsulphosuccinamates,
    alkylsulphoacetates,
    acylsarcosinates, acylpolypeptidates, acylamidopolypeptidates, acylisethionates, N-acyltaurates;
    the alkyl and acyl radicals containing 8 to 18 carbon atoms;
  b) fatty acid salts and acyl($C_8$-$C_{20}$)lactylates.

13. Composition according to claim 11, characterised in that the nonionic surfactant is chosen from:
  a) polyoxyethylenated, polypropoxylated or polyglycerolated alcohols, alkylphenols or fatty acids containing a fatty chain containing 8 to 18 carbon atoms and containing 2 to 50 ethylene oxide or propylene oxide groups or 2 to 30 glycerol groups;
  b) copolymers of ethylene and propylene oxide, condensates of ethylene and propylene oxide with fatty alcohols, polyoxyethylenated fatty amides, polyoxyethylenated fatty amines, ethanolamides, glycol fatty acid esters, sorbitan fatty acid esters, oxyethylenated or otherwise, sucrose fatty acid esters, polyethylene glycol fatty acid esters, fatty acid esters of glucose derivatives, amine oxides;
  c) the compounds of formula (IV):

in which $R_4$ denotes a radical or a mixture of alkyl radicals containing 10 to 14 carbon atoms and m is a whole or decimal number from 2 to 10 and preferably from 3 to 6;

d) the compounds of formula (V):

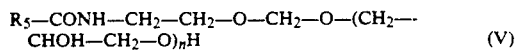

in which $R_5$ denotes an alkyl and/or alkenyl radical containing from 11 to 17 carbon atoms or a mixture of such radicals and n denotes a whole or decimal number from 1 to 5 and preferably 1.5 to 4;

e) the compounds of formula (VI):

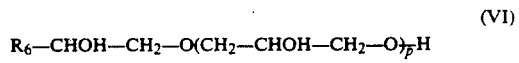

in which $R_6$ denotes an aliphatic, cycloaliphatic or arylaliphatic radical preferably containing 7 to 21 carbon atoms, and mixtures thereof, the aliphatic chains denoting in particular alkyl chains which may contain 1 to 6 ether, thioether and/or hydroxymethylene groups, and p is between 1 and 10 inclusive;

f) the compounds obtained by condensation, using acidic catalysis, of 2 to 10 and preferably 2.5 to 6 moles of glycidol per mole of $C_{10}$-$C_{14}$ alcohol or alphadiol;

g) the poly(hydroxypropyl)ethers obtained by polyaddition of glycerol monochlorohydrin to a (poly)-hydroxylated organic compound in the presence of a strong base.

14. Composition according to claim 13, in which the nonionic surfactant is chosen from:
  ($\alpha$) the compounds corresponding to the following formulae (VII) and (VIII):

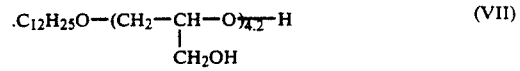

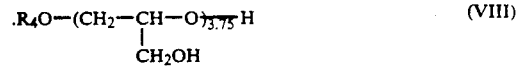

in which $R_4$ denotes a mixture of $C_{10}H_{21}$ and $C_{12}H_{25}$ alkyl radicals;

($\beta$) the compounds prepared by condensation, using alkaline catalysis, of 3.5 moles of glycidol with an alpha-diol containing 12 carbon atoms;

($\gamma$) the compounds corresponding to the formula:

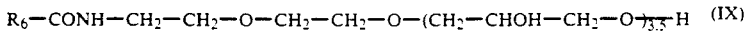

where $R_6$ denotes a mixture of radicals containing the following alkyl and alkenyl radicals: $C_{11}H_{23}$, $C_{13}H_{27}$, the radicals derived from copra fatty acids and the radical derived from oleic acid;

(δ) the compounds prepared by condensing 3.5 moles of glycidol with a mixture of $C_{11}$–$C_{14}$ alpha-diols;

(ε) the compound prepared by condensing 2.5 moles of glycerol monochlorohydrin with 1,2-dodecanediol in the presence of sodium hydroxide.

15. Composition according to claim 11, in which the additional amphoteric or zwitterionic surfactant is chosen from:
a) derivatives of aliphatic secondary or tertiary amines, in which the aliphatic radical is a linear or branched chain of 6 to 18 carbon atoms and containing at least one water-soluble carboxylic, sulphonate, sulphate, phosphate or phosphonate anionic group;
b) alkyl ($C_{10}$–$C_{20}$)betaines, sulphobetaines, amidoetaines and amidosulphobetaines.

16. Composition according to claim 15, in which the amphoteric surfactants are chosen from the compounds of formula:

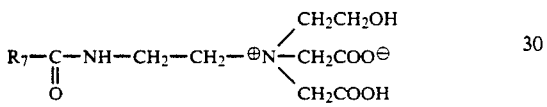

in which $R_7$ denotes an alkyl radical derived from copra, a heptyl, nonyl or undecyl radical; or the compounds of formula:

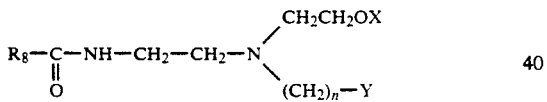

in which:
n = 1 or 2;
X denotes the —$CH_2CH_2COOH$ group or hydrogen;
Y denotes —COOH or the radical

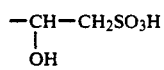

$R_8$ denotes an alkyl radical derived from copra, a $C_7$, $C_9$, $C_{11}$ or $C_{13}$ alkyl radical, a $C_{17}$ alkyl radical and its iso form, an unsaturated $C_{17}$ radical, or an alkyl radical derived from linseed oil.

17. Composition according to claim 1, characterised in that it contains a mixture of anionic surface-active agents and of amphoteric or zwitterionic surface-active agents which represent up to 50% and preferably 5 to 30% total weight of the surface-active agents.

18. Composition according to claim 11, characterised in that it contains a mixture of anionic surface-active agents and of nonionic surface-active agents which represent up to 80% and preferably 5 to 50% of the total weight of the surface-active agents.

19. Composition according to claim 1, characterised in that it is in the form of a clear product and in that the compound of formula (I) is chosen from those in which:

A denotes hydrogen, R denotes nonylphenyl, n has the value 7 and p is equal to 0, and mixtures of compounds of formula (I), in which:
A denotes hydrogen, R denotes lauryl, n has the value 10 and p is equal to 0; R denotes octylphenyl, n has the value 4 or 8, p is equal to 0 and A denotes hydrogen.

20. Composition according to claim 1, which is opaque product and in which the compound of formula (I) is chosen from those in which:
A denotes hydrogen, R denotes octylphenyl, n has the value 4 and p has the value 0;
A denotes hydrogen, R denotes nonylphenyl, n has the value 4 and p has the value 0;
A denotes hydrogen, R denotes oleyl, n has the value 2 or 5, and p has the value 0;
A denotes hydrogen, R denotes $C_{12}$–$C_{14}$ alkyl, n has the value 2.5 and p has the value 0.

21. A clear composition according to claim 19, characterised in that the silicone is chosen from
cyclic volatile silicones containing 3 to 7 silicon atoms or their mixtures with organosilicon compounds;
linear polydimethylsiloxane oils containing 2 to 9 silicon atoms, which have a viscosity lower than $2 \times 10^{-6}$ m²/s;
polyphenylmethylsiloxane oils with a viscosity lower than $5 \times 10^{-5}$ m²/s.

22. An opaque composition according to claim 20, in which the silicone is chosen from:
silicone oils with a viscosity of between 0.2 and 2.5 m²/s at 25° C.;
mixtures of organopolysiloxanes and of cyclic silicones;
mixtures of two polydimethylsiloxanes of different viscosities;
modified organopolysiloxanes of formulae (II) or (III), as defined in claim 6.

23. Composition according to claim 11, characterised in that the concentration of additional surfactant does not exceed 40% of the total weight of the composition.

24. Composition according to claim 11, characterised in that it exhibits a pH of between 2 and 9.

25. Composition according to claim 1, characterised in that it is in the form of a thickened liquid, gel or aerosol foam.

26. Composition according to claim 1, characterised in that it additionally contains a viscosity-regulating agent present in a concentration which may range up to 15% by weight relative to the total weight of the composition.

27. Composition according to claim 1, characterised in that it additionally contains agents for conditioning hair or the skin, which are chosen from cationic surface-active agents, anionic or cationic or amphoteric polymers, quaternised or unquaternised proteins and water-soluble silicones, which do not alter the stability of the composition.

28. Composition according to claim 27, characterised in that water-soluble silicones are present in proportions ranging up to 10% by weight relative to the total weight of the composition.

29. Composition according to claim 27, characterised in that the cationic or anionic or amphoteric polymers, the cationic agents or the quaternised or unquaternised proteins are present in proportions of between 0.01 and 6% by weight relative to the total weight of the composition.

30. Composition according to claim 1, additionally containing adjuvants chosen from sequestering agents, perfumes, colorants, stabilisers, foam stabilisers, propelling agents, alkalifying or acidifying agents or other adjuvants usually employed in cosmetics.

31. Process for washing and conditioning hair or the skin, characterised in that a composition as defined according to claim 1 is applied to these, this application being followed by rinsing.

32. A composition according to claim 5, in which the linear polydimethylsioxanes (A) have a viscosity of from $10^{-5}$ to 1 m$^2$/s.

33. A composition according to claim 8, characterized in that the silicone is present in proportions of between 0.2 and 10% by weight relative to the total weight of the composition.

34. A composition according to claim 26 in which the viscosity-regulating agent is an electrolyte, a hydrotrope or other thickener.

35. A composition according to claim 28, characterized in that the water-soluble silicones are present in a proportion between 0.5 and 6% by weight relative to the total weight of the composition.

* * * * *